United States Patent [19]

Winkler

[11] Patent Number: 4,470,982

[45] Date of Patent: Sep. 11, 1984

[54] SHAMPOO COMPOSITIONS

[75] Inventor: William M. Winkler, Cincinnati, Ohio

[73] Assignee: The Procter & Gamble Company, Cincinnati, Ohio

[21] Appl. No.: 367,204

[22] Filed: Apr. 12, 1982

Related U.S. Application Data

[63] Continuation of Ser. No. 219,281, Dec. 22, 1980, abandoned, which is a continuation-in-part of Ser. No. 119,283, Feb. 7, 1980, abandoned.

[51] Int. Cl.$^3$ .................. A61K 31/555; A61K 33/04; A61K 31/615; A61K 31/61
[52] U.S. Cl. .................... 424/245; 424/164; 424/233; 424/234; 424/263
[58] Field of Search .......................... 424/245

[56] References Cited

U.S. PATENT DOCUMENTS

| | | | |
|---|---|---|---|
| 2,786,847 | 3/1957 | Cislak | 260/294.8 |
| 2,809,971 | 10/1957 | Bernstein et al. | 260/270 |
| 3,476,489 | 11/1969 | Mees et al. | 424/164 |
| 3,489,686 | 1/1970 | Parran | 252/106 |
| 3,583,999 | 6/1971 | Damico | 260/294.8 G |
| 3,590,035 | 6/1971 | Damico | 260/290 |
| 3,773,770 | 11/1973 | Damico | 260/290 R |
| 3,785,985 | 1/1974 | Grand | 252/106 |
| 3,917,817 | 11/1975 | Vanlerberghe | 424/70 |
| 4,033,895 | 7/1977 | Gerstein | 252/106 |
| 4,041,033 | 8/1977 | Douglass | 260/250 A |
| 4,089,945 | 5/1978 | Brinkman et al. | 252/164 |
| 4,161,526 | 7/1979 | Gorman | 424/245 |
| 4,323,683 | 4/1982 | Bolich et al. | 546/6 |

FOREIGN PATENT DOCUMENTS

| | | |
|---|---|---|
| 2060810 | 5/1977 | Japan . |
| 1051268 | 12/1966 | United Kingdom . |
| 1280671 | 7/1972 | United Kingdom . |
| 1290602 | 9/1972 | United Kingdom . |
| 1390078 | 4/1975 | United Kingdom . |

OTHER PUBLICATIONS

Inorganic Chemistry 16, 1834, (1977), Suave® Antidandruff Shampoo.

Primary Examiner—Frederick E. Waddell
Attorney, Agent, or Firm—Richard C. Witte; John V. Gorman; Douglas C. Mohl

[57]     ABSTRACT

Antidandruff, lotion shampoo compositions which contain critical amounts of an anionic surfactant, a suspending agent and an alkanol amide.

8 Claims, No Drawings

SHAMPOO COMPOSITIONS

CROSS-REFERENCE TO RELATED APPLICATION

This is a continuation of application Ser. No. 219,281, filed Dec. 22, 1980 now abandoned, which is a continuation-in-part application of application Ser. No. 119,283, filed Feb. 7, 1980, now abandoned.

TECHNICAL FIELD

The present invention is related to antidandruff lotion shampoo compositions which possess good lotion viscosity while also being quite stable with respect to separation.

Lotion compositions, particularly those containing particulate materials, traditionally suffer from liquid separating. If an attempt is made to avoid such separation the compositions become too viscous for satisfactory pouring. A totally acceptable product requires that both stability and viscosity be optimized.

BACKGROUND ART

The separate use of the components of the present invention in shampoos is known in the shampoo art.

U.S. Pat. No. 3,917,817, Nov. 5, 1975 to Vanlerberghe et al discloses a shampoo composition containing a piperazine based cationic polymer, 10% sodium alkyl sulfate, 4% lauryl monoethanolamide and 3% glycol distearate. U.S. Pat. No. 4,013,787, Mar. 22, 1977 to Vanlerberghe et al discloses a similar composition. Japanese Application, with Open for Public Inspection No. 60810, May 19, 1977 (Lion Fat & Oil), discloses shampoos containing 5% to 50% of an anionic surfactant, 1% to 10% of a fatty acid diethanol amide, 0.1% to 10% of an insoluble fine powder, and 1% to 10% of an ethyleneglycol ester.

While these references disclose compositions which contain components of the type present in the compositions of the present invention, they do not suggest combining the components in the amounts found critical by the present inventor.

It is an object of the present invention, therefore, to provide shampoos containing certain critical levels of surfactant, amide and a suspending agent as well as containing a particulate antidandruff agent.

It is a further object of the present invention to provide shampoos which have optimal viscosity and liquid separation.

These and other objectives will become readily apparent from the detailed description which follows.

DISCLOSURE OF THE INVENTION

The present invention relates to antidandruff shampoo compositions comprising from about 11% to about 20% of an anionic surfactant, from about 4% to about 6% of a suspending agent, from about 2% to about 4% of an alkanol amide, a particulate antidandruff agent and water. The compositions exhibit very little liquid separation and preferably have a viscosity at 25° C. of from about 2500 cps to about 6000 cps.

DETAILED DESCRIPTION OF THE INVENTION

The compositions of the present invention comprise certain essential components and may additionally contain several optional components. Each of the components is discussed in detail below.

Anionic Surfactant

The surfactant in the shampoos of this invention is anionic and is present at a level of from about 11% to about 20%, preferably about 14% to about 18%. Specifically, the surfactant is an alkyl sulfate, an ethoxylated alkyl sulfate or mixtures thereof. The alkyl sulfates found useful are the sodium, ammonium and triethanolamine alkyl sulfates having from about 8 to about 22 carbon atoms in the alkyl chain. Preferred are those sulfates obtained by sulfating the higher alcohols, those having from about 8 to about 18 carbon atoms.

The ethoxylated alkyl sulfates have alkyl chains of the type used with the alkyl sulfates but have from about 1 to 6, preferably 3, ethoxy groups per molecule.

The most preferred surfactant is sodium alkyl sulfate. With this surfactant, as well as others, the viscosity may be controlled in the desired range by the total amount of buffering agent which may be present.

Suspending Agent

The suspending agent useful in the present compositions can be any of several materials. Included are ethylene glycol esters of fatty acids having from about 16 to about 22 carbon atoms. Preferred are the ethylene glycol stearates, both mono and distearate. Other suspending agents found useful are alkanol amides of fatty acids, having from about 16 to about 22 carbon atoms, preferably about 16 to 18 carbon atoms. Preferred alkanol amides are stearic monoethanolamide, stearic diethanolamide, stearic monoisopropanolamide and stearic monoethanolamide stearate.

Still other suitable suspending agents are alkyl ($C_{16-22}$) dimethyl amine oxides such as stearyl dimethyl amine oxide. Mixtures of these materials are also acceptable.

The suspending agent is present at a level of from about 4% to about 6%. The suspending agent serves to assist in suspending the antidandruff active and may give pearlescence to the product.

Amide

The amide used in the present compositions can be any of the alkanolamides of fatty acids known for use in shampoos. These are generally mono- and diethanolamides of fatty acids having from about 8 to about 14 carbon atoms. Preferred are coconut monoethanolamide, lauric diethanolamide and mixtures thereof.

The amide is present at a level of from about 2% to about 4%.

Antidandruff Agent

Another essential element of the present compositions is a particulate antidandruff agent. Included among such agents are sulfur, selenium sulfide, salicylic acid, zinc pyridinethione, other 1-hydroxy pyridones, such as those disclosed in U.S. Pat. No. 4,185,106, Jan. 22, 1980 to Dittmar et al, incorporated herein by reference and azole antimycotics disclosed in British Pat. No. 1,502,144, Feb. 22, 1978, incorporated herein by reference, among many others. The antidandruff agent is present at a level of from about 0.2% to about 4%.

Zinc pyridinethione is the preferred agent, particularly where its salt crystals are predominantly flat platelets which have a mean sphericity less than about 0.65, preferably between about 0.20 and about 0.65, and a median particle diameter of at least about 2μ, expressed as the diameter of a sphere of equivalent volume. It is preferred that the median particle diameter not be greater than about 15μ, expressed on the same basis.

The diameter of a sphere of equivalent volume, $d_v$, for a particle can be determined by a variety of sedimentation techniques which are based on Stokes' Law for the settling velocity of a particle in a fluid. Such techniques are described in Stockham, J. D. and Fochtman, E. G., *Particle Size Analysis*, Ann Arbor Science, 1978, incorporated herein by reference.

The sphericity of a particle is also described by Stockham and Fochtman at page 113 as $$\psi = \left(\frac{d_v}{d_s}\right)^2$$

where $d_v$ is the diameter of a sphere of equivalent volume, supra, and $d_s$ is the diameter of a sphere of equivalent area. A technique for determining $d_s$ is the BET technique described by Stockham and Fochtman at page 122.

Since the sphericity of interest herein is the mean sphericity, the mean diameters are employed.

Water

The compositions of the present invention are lotions with water being the major carrier. The amount of water present is generally from about 35% to about 90%, preferably from about 60% to about 80%.

Optional Components

The shampoos herein can contain a variety of nonessential optional ingredients suitable for rendering such compositions more stable and desirable. Such conventional optional ingredients are well known to those skilled in the art, e.g., preservatives such as benzyl alcohol, methyl paraben, propyl paraben and imidazolidinyl urea; pH adjusting agents such as citric acid, sodium citrate, succinic acid, phosphoric acid, sodium hydroxide, sodium carbonate, etc.; and, sequestering agents such as disodium ethylenediamine tetraacetate.

Minor ingredients such as perfumes, dyes and coloring agents can also be added to the instant compositions to improve their consumer acceptability. If present, such agents generally comprise from about 0.1% to 2.0% by weight of the composition.

The shampoos of the present invention are preferably substantially free of suspending agents such as magnesium/aluminum silicate (present at less than about 0.1%) and inorganic salts such as alkali metal chlorides and ammonium chloride (present at less than about 0.70%). Additionally while the pH may be in the range of from about 3 to about 9, the preferred pH is from about 4 to about 6, particularly when ammonium alkyl sulfate is the surfactant. The proper pH is obtained through the use of an appropriate buffer such as sodium citrate/citric acid.

Method of Manufacture

The shampoos of the present invention may be made using mixing techniques well known in the art.

Industrial Applicability

The shampoos of the present invention are used in a conventional manner.

The following examples further describe and demonstrate embodiments within the scope of the present invention. The exammples are given solely for the purpose of illustration and are not to be construed as limitations of the present invention as many variations thereof are possible without departing from its spirit and scope. Unless otherwise indicated, all percentages herein are by weight.

EXAMPLE I

A shampoo composition of the present invention having the following composition was prepared.

| Component | Level |
| --- | --- |
| Ammonium Alkyl Sulfate (27% Aqueous Solution) | 55.25% |
| Citric Acid | 0.24 |
| Sodium Citrate | 0.55 |
| Coconut Monoethanolamide | 3.00 |
| Ethylene Glycol Distearate | 5.00 |
| Zinc Pyridinethione | 2.00 |
| Methyl Paraben | 0.20 |
| Propyl Paraben | 0.10 |
| Color Solution | 0.20 |
| Perfume | 0.50 |
| Water q.s. | 100.00% |

The composition had a viscosity of about 4000 cps and experienced very little separation after 2 weeks at 120° F.

EXAMPLE II

The following shampoo composition was prepared.

| Component | Level |
| --- | --- |
| Ammonium Alkyl Sulfate (27% Aqueous Solution) | 55.25% |
| Coconut Monoethanolamide | 3.0 |
| Ethylene Glycol Distearate | 5.0 |
| Zinc Pyridinethione | 2.0 |
| Ammonium Chloride | 1.0 |
| Citric Acid | 0.24 |
| Sodium Citrate | 0.55 |
| Methyl Paraben | 0.20 |
| Propyl Paraben | 0.10 |
| Color | 0.15 |
| Perfume | 0.50 |
| Water | q.s. |
|  | 100.00 |

This formulation, which contains a level of ammonium chloride outside the scope of the present invention, separated unacceptably after 1 week at 100° F.

EXAMPLE III

The following composition was prepared.

| Component | Level |
| --- | --- |
| Ammonium Alkyl Sulfate (27% Aqueous Solution) | 55.25% |
| Zinc Pyridinethione | 2.00 |
| Coconut Monoethanolamide | 4.64 |
| Ethylene Glycol Distcarate | 2.35 |
| Citric Acid | 0.20 |
| Methyl Paraben | 0.20 |
| Propyl Paraben | 0.10 |
| Color Solution | 0.35 |
| Perfume | 0.50 |
| Water | q.s. 100.00% |

This composition, outside the scope of the present invention, had an acceptable viscosity of 5,520 cps but showed unacceptable liquid separation at 100° F. after 1 month.

What is claimed is:

1. A lotion shampoo composition comprising:
   (A) from about 11% to about 20% of a surfactant selected from the group consisting of alkyl sulfates, ethoxylated alkyl sulfates and mixtures thereof;
   (B) from about 4% to about 6% of a suspending agent selected from the group consisting of ethylene glycol esters of fatty acids having from about 16 to about 22 carbon atoms, alkanol amides of fatty acids having from about 16 to about 22 carbon atoms, alkyl ($C_{16-22}$) dimethyl amine oxides and mixtures thereof;
   (C) from about 2% to about 4% of an alkanolamide of a fatty acid having from about 8 to about 14 carbon atoms;
   (D) from about 0.2% to about 4% of a particulate antidandruff agent; and
   (E) from about 35% to about 90% water,
   wherein said composition is substantially free of alkali metal chlorides and ammonium chloride.

2. A shampoo composition according to claim 1 wherein the surfactant is selected from the group consisting of ammonium alkyl sulfate, sodium alkyl sulfate, sodium ethoxy(3)alkyl sulfate, triethanolamine alkyl sulfate and mixtures thereof.

3. A shampoo composition according to claim 2 wherein the suspending agent is selected from the group consisting of ethylene glycol monostearate, ethylene glycol distearate and mixtures thereof.

4. A shampoo composition according to claim 3 wherein the alkanolamide of a fatty acid having from about 8 to about 14 carbon atoms is selected from the group consisting of coconut monoethanolamide, lauric diethanolamide and mixtures thereof.

5. A shampoo composition according to claim 4 wherein the surfactant is sodium alkyl sulfate wherein the alkyl group contains from about 8 to about 18 carbon atoms and wherein the pH of said composition is from about 4 to about 6.

6. A shampoo composition according to claim 5 wherein the alkanolamide is coconut monoethanolamide.

7. A shampoo composition according to claim 6 wherein the suspending agent is ethylene glycol distearate;

8. A shampoo composition according to claim 7 wherein the antidandruff agent is zinc pyridinethione.

* * * * *